United States Patent [19]

DesMarais

[11] 4,425,130
[45] Jan. 10, 1984

[54] COMPOUND SANITARY NAPKIN

[75] Inventor: Thomas A. DesMarais, Norwood, Ohio

[73] Assignee: The Procter & Gamble Company, Cincinnati, Ohio

[21] Appl. No.: 273,122

[22] Filed: Jun. 12, 1981

[51] Int. Cl.$^3$ .............................................. A61F 13/16
[52] U.S. Cl. .................................... 604/389; 604/385; 604/358
[58] Field of Search .......... 128/156, 284, 287, 290 R, 128/290 W, 290 P, 296; 604/358, 367, 370–372, 378, 383, 389

[56] References Cited

U.S. PATENT DOCUMENTS

| | | | |
|---|---|---|---|
| 2,295,016 | 9/1942 | Scribner . | |
| 2,683,457 | 7/1954 | Cunningham . | |
| 2,929,379 | 3/1960 | Poulsen | 128/290 R |
| 2,965,102 | 12/1960 | Harwood . | |
| 3,183,909 | 5/1965 | Roehr . | |
| 3,406,689 | 10/1968 | Hicks et al. | 128/290 R |
| 3,512,530 | 5/1970 | Jones, Sr. | 128/290 R |
| 3,570,492 | 3/1971 | Bettencourt | 128/290 R |
| 3,886,941 | 6/1975 | Duane et al. | 128/156 |
| 4,041,951 | 8/1977 | Sanford | 128/290 W |
| 4,289,130 | 9/1981 | Usami et al. | 128/287 |
| 4,341,217 | 7/1982 | Ferguson et al. | 128/290 W |

FOREIGN PATENT DOCUMENTS

1211095 11/1970 United Kingdom ................ 128/287

Primary Examiner—C. Fred Rosenbaum
Assistant Examiner—Sherri Vinyard
Attorney, Agent, or Firm—Monte D. Witte; Fredrick H. Braun; Richard C. Witte

[57] ABSTRACT

Compound sanitary napkins comprising a primary menstrual pad and a panty protector joined by union means having limited extent. The primary menstrual pad comprises an absorbent core and, optionally, a pad overwrap and, also optionally, a fluid barrier. The panty protector comprises an absorbent element and a moisture barrier and, optionally, a protector overwrap and, also optionally, adhesive attachment means. The two constituents are joined at their corresponding ends, with the absorbent element of the panty protector interposed between the moisture barrier of the panty protector and the primary menstrual pad, by the union means in such a manner that the two are free to move relative to one another along essentially their entire common length. In use, the compound sanitary napkin is secured to the user's undergarments (as by the optional adhesive attachment means) in such a position that the primary menstrual pad is interposed between the panty protector and the user's body.

24 Claims, 5 Drawing Figures

COMPOUND SANITARY NAPKIN

BACKGROUND OF THE INVENTION

1. Field of the Invention

This invention concerns disposable sanitary napkins. As used herein, sanitary napkins are considered to be absorbent devices designed to be worn externally of the body by woven, usually during their menstrual periods, and to receive and contain menses and other vaginal discharges. Disposable sanitary napkins are intended to be disgarded after use and soiling rather than being cleaned and reused.

2. Background Art

Disposable sanitary napkins are staple items of modern society. In their simplest form they comprise an absorbent element interposed between a pervious body contacting element and an impervious protective barrier. The absorbent element is, of course, intended to receive and contain menses and other vaginal discharges. The body-containing element (sometimes called a topsheet or an overwrap) is intended to provide more or less comfortable and dry-feeling contact with body surfaces while allowing free passage of fluids therethrough into the absorbent element. The protective barrier is intended to prevent menses or other vaginal discharges which are expelled or which escape from the absorbent element from soiling the user's garments.

In addition to the three functional elements mentioned above, disposable sanitary napkins are generally provided with means for supporting the device adjacent the user's crotch area, even as the user moves, where it can most effectively perform its intended function. Traditionally, this support means has involved the use of waist encircling belts having suspenders depending from the front and rear thereof. These suspenders are of various designs and are provided with means of various designs for securing the sanitary napkins thereto.

More recently, sanitary napkins have been provided with adhesive attachment means for securing the device to the inner crotch area of the user's undergarments. Elimination of the traditional belt is generally considered to be a definite advance in sanitary napkin technology.

Usually, sanitary napkins are unitary structures of generally rectangular or oval shape having a greater or lesser thickness depending on the particular design. U.S. Pat. Nos. 595,861, 2,625,161, and 3,111,948, for example, illustrate conventional types of sanitary napkins.

As noted, the usual sanitary napkin presents the appearance of and performs as a unitary (i.e. one piece) device. While certain sanitary napkin designs involve two absorbent elements (as described in, for example, U.S. Pat. No. 2,965,102 issued to Harwood on Dec. 20, 1960) or two separable units (as described in, for example, U.S. Pat. No. 2,683,457 issued to Cunningham on July 13, 1954), they perform as unitary devices.

While previously known sanitary napkins do perform their intended function, each conventional design suffers from certain deficiencies in one or more of absorbency of body fluids, protection of the user's garments from soiling, and physical comfort to the user.

One species of sanitary napkin which has gained popularity in recent times is sometimes referred to as a mini-pad or panty shield. These particular devices are generally no more than conventional sanitary napkins in which the bulk and, therefore, the fluid capacity of the absorbent element has been drastically reduced as compared to conventional sanitary napkins. They are usually provided with adhesive attachment means. Such devices are generally perceived by the user as having enhanced wearing comfort, but their drastically reduced absorbent capacity makes them useful only when menstrual flows are small an impractical for use throughout the menstrual cycle.

SUMMARY OF THE INVENTION

The present invention is of a compound sanitary napkin comprising a panty protector and a primary menstrual pad joined by union means having limited extent. The panty protector comprises an adsorbent element and a moisture barrier while the primary menstrual pad comprises an absorbent core. Optionally, both the panty protector and the primary menstrual pad comprise fluid permeable overwraps. Optionally, the panty protector comprises an adhesive attachment means. Optionally, the primary menstrual pad comprises a fluid barrier.

Accordingly, it is an object of this invention to provide compound sanitary napkins having enhanced absorbency, garment protection, and comfort as compared to conventional sanitary napkins having the same, or even greater, amounts of absorbent material.

BRIEF DESCRIPTION OF THE DRAWINGS

To aid in the understanding of the invention, the following non-limiting drawings, in which the thickness of certain materials has been exaggerated for clarity, are presented.

Reference numerals are used consistently in the drawings.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the appended drawings and examples.

This invention is of a compound sanitary nakpin which exhibits absorbency for bodily fluids, protection of the user's garments from soiling, and physical comfort to the user. These attributes are superior to those of conventional sanitary napkins having equivalent, or even greater, amounts of absorbent material.

The compound sanitary napkin of this invention comprises a panty protector and a primary menstrual pad joined by union means having limited extent. FIGS. 1, 2, 3, and 4 are of one embodiment of compound sanitary napkin 10 and illustrate primary menstrual pad 30, panty protector 20, and union means having limited extent 40.

The primary menstrual pad is, at its name implies, that constituent of the compound sanitary napkin intended to absorb the bulk of the bodily fluids discharged by the user. The primary menstrual pad comprises an absorbent core. Optionally, it can comprise a pad overwrap. Optionally, it can comprise a fluid barrier. In the figures, reference numerals 31, 32 and 33, respectively, refer to these components.

Because the compound sanitary napkin is designed to absorb bodily fluids, principally menses and other vaginal discharges, the absorbent core must be constructed of a material which readily absorbs such fluids. In general, the absorbent core comprises a material which is wetted by the fluids in question. Since menses and other bodily fluids are primarily aqueous solutions, materials which are wetted by these fluids can be broadly described as hydrophilic. Unless otherwise indicated, as used in this specification the term "hydrophilic" describes materials and surfaces which are wetted by the fluid in question. Thus, the absorbent core must be hydrophilic.

The state of the art respecting wetting of materials allows definition of hydrophilicity (and wetting) in terms of contact angles and the surface tensions of the fluids and solids involved. This is discussed in detail in the American Chemical Society Publication entitled *Contact Angle, Wettability and Adhesion* edited by Robert F. Gould, and copyrighted in 1964, said publication being herein incorporated by reference. A surface is said to be wetted by a fluid either when the contact angle between the fluid and the surface is less than 90° or when the fluid will tend to spread spontaneously across the surface; both conditions normally coexist.

Menses normally has a surface tension of from about 35 to about 60 dynes per centimeter. It will have a contact angle of less than 90° and will tend to spread spontaneously across a solid which has a critical surface tension value greater than the fluid surface tension. Since the surface tension of water is higher than that of menses, any solid which is wetted by water (i.e. which is literally hydrophilic in the precise, limited meaning of the word) is also usually wetted by menses.

The material used in the absorbent core can achieve hydrophilicity by any convenient means. For example, the material itself can be intrinsically hydrophilic. Alternatively, the material can be provided with a finish which renders its surface hydrophilic. Another method of rendering the material hydrophilic is to treat it with a surfactant, such as a nonionic or anionic surfactant, as by spraying the material with the surfactant or dipping the material into the surfactant.

One example of a suitable material of construction for the absorbent core comprises airlaid wood pulp fibers. These fibers, sometimes known as communition grade wood pulp fibers, are fibers which have been liberated from the wood by any convenient means and dried, likewise by any convenient means. The resulting sheets of fibers are then comminuted to produce essentially intact individual fibers in a gaseous stream from which the fibers are then formed into an absorbent batt. Such absorbent batts are well known to those skilled in the diaper, bandage, and sanitary napkin art. Absorbent cores formed from such batts, as well as those described hereinafter, can be of greater thickness in the middle regions than at the ends or edges or both ends and edges.

Alternatively, but less preferably, the absorbent core can be made from an absorbent foam material such as cellulose foam or polyurethane foam. The latter, for example, can be made according to the teachings of U.S. Pat. No. 4,067,832 which issued to DesMarais on Jan. 10, 1978. Another useful foam material is the polyester foam made according to the teachings of U.S. Pat. No. 4,110,276 which issued to DesMarais on Aug. 29, 1978. (Both of the preceding noted patents are herein incorporated by reference.)

Cellulose wadding as sometimes used in disposable diapers can also be used to construct the absorbent core.

Another material from which the absorbent core can be constructed comprises an unbonded array of non-absorbent, hydrophilic, resilient, moisture insensitive fibers. Such an array can be formed by airlaying, carding, or any means of random placement of fibers. Nonabsorbent fibers are those fibers which will absorb within the fiber itself no more than about 6% (by weight of the fiber) moisture when maintained at 21° C. and 65% relative humidity for 24 hours. The term moisture insensitive is used herein to describe fibers whose resiliency is relatively uneffected by the presence of moisture. Fibers are said to be moisture insensitive when their initial modulus in the presence of moisture is at least about 90% of the initial dry state modulus. (Initial modulus can be measured according to A.S.T.M. Standard Method D3822 "Standard Test Method for Textile Properties of Single Textile Fibers.") Resiliency is the intrinsic property of a fiber which allows the individual fiber to resist physical deformation or, conversely, which causes the fiber to tend to resume its original configuration after deformation such as elongation. Resiliency of fibers can be described by the initial modulus of the fibers. To be useful herein, the fiber should have an initial modulus greater than about 30 grams per denier. Examples of useful fibers include polypropylene fibers sold under the designation C-01-S-021 by Philips Petroleum Corp. of Bartlesville, Oklahoma; fibers sold under the orlon trademark (such as type 72 Orlon) by E. I. DuPont DeNemours Incorporated of Wilmington, Delaware; those sold under the Kevlar trademark by DuPont; those sold under the Kodel trademark by Eastman Chemical Products, Inc. of Kingsport, Tennessee; and polyester fibers. As noted, the surface of the fibers should be hydrophilic. Hydrophilicity can be imparted to the fibers by surfactant treatment as discussed above. A specific surfactant having use in this application is Pluronic L92, nonionic surfactant having molecular weight of about 3,600 and a hydroxyl number of about 31 as made by BASF Wyandotte of Wyandotte, Michigan.

Preferably, the absorbent core is made from airlaid mixed softwood fibers and has a density of from about 0.003 to about 0.09 gram per cubic centimeter.

Optionally, the absorbent core can contain ancillary absorbent material which tends to increase its absorbent capacity. Ancillary materials such as the bibulous cellulosic fibers described in U.S. Pat. No. 3,589,364 which issued to Dean et al on June 29, 1971 and the substantially insoluble acidic carboxymethyl cellulose products shown in U.S. Pat. No. 3,678,031 which issued to Schoggen on July 18, 1972 can be used effectively. (Both of the aforementioned patents are herein incorporated by reference.)

Optionally, and preferably, the primary menstrual pad is provided with pad overwrap 32 as shown in the figures. This pad overwrap can be any fluid permeable material commonly used as an overwrap in sanitary napkins or as a topsheet in disposable diapers. Useful materials include carded, spun-bonded, melt blown web, airlaid webs, and other non-woven webs of natural or synthetic fibers. Apertured and embossed and apertured continuous thermoplastic films are also useful.

Preferably, the pad overwrap is hydrophobic so that bodily fluids will not normally remain on the overwrap surface, thereby presenting a drier feel to the user. The pad overwrap must be able to remain in contact with sensitive areas of the human body without causing irritation.

One preferred pad overwrap comprises an apertured hydrophobic film (such as a thermoplastic film of, e.g. polyethylene) having a caliper or less than about 0.075 centimeter, an open area of at least about 35%, and being provided with irregular apertures less than about 25% of which have an equivalent hydraulic diameter smaller than or equivalent to 0.064 centimeter. (Equivalent hydraulic diameter is defined as four times the quotient of the area of the aperture divided by its perimeter.) Optionally, the surface of the overwrap oriented toward the absorbent core can be provided with a thin layer of uniformly distributed fibers, such as polyester, rayon, wood pulp, or cotton fibers, which preferably are less hydrophobic than the pad overwrap.

Another preferred pad overwrap is made from a fluid impermeable material such as a thermoplastic film (for example polyethylene film) which is provided with a multiplicity of protuberances projecting from the plane of the pad overwrap toward the absorbent core, which protuberances have a base in the plane of the pad overwrap and an apex remote from that plane. Both the apex and the base of essentially each proturberance are apertured. The opening may be circular or irregularly shaped. Preferably, the maximal diagonal of the largest apex opening is from about 0.025 centimeter to about 0.25 centimeter. (For rectilinear shapes, the maximal-diagonal is the longest line which can be drawn between two non-adjacent verticies of the shape. For curvilinear shapes, the maximal diagonal is the largest diameter of the shape.) The maximum diagonal of the base opening is equal to or greater than the maximal diagonal of the apex opening. The protuberances may be formed by using any of several different methods well known in the art. For example, the apparatus disclosed in U.S. Pat. No. 4,151,240 which issued to Lucas et al on Apr. 4, 1979 (which patent is herein incorporated by reference) can be used. The caliper, i.e. the thickness of the sheet after the protuberances have been formed as measured from the base to the apex of the protuberance, can be from about 0.033 centimeter to about 0.089 centimeter.

Figure 5:
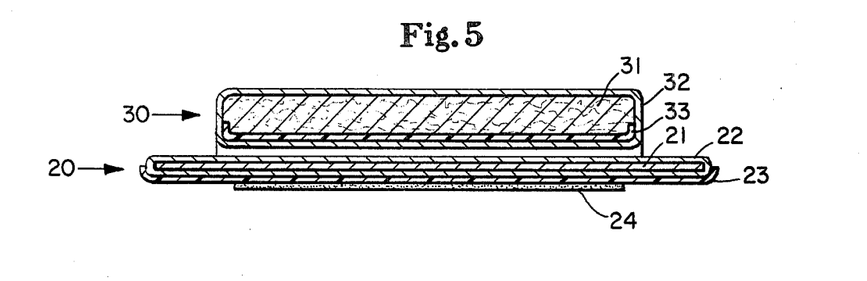
FIG. 5 is a cross sectional view analogous to that shown in FIG. 3, but of a different embodiment of the compound sanitary napkin of this invention.

Optionally, the primary menstrual pad can comprise a fluid barrier 33 as illustrated in FIG. 5. This fluid barrier tends to contain absorbed fluids within the absorbent core and can be constructed from materials having the same properties as the panty protector moisture barrier described hereinafter.

The length and width of the primary menstrual pad can be of any convenient character. While it can be generally circular or oval in its unstressed cross-sectional shape, it is preferably rectangular in cross-section. For example, the primary menstrual pad, can be from about 15 to about 25 centimeters long, and from about 3 to about 6 centimeters in width.

The second necessary constituent of the compound sanitary napkin of this invention is the panty protector.

The panty protector comprises an absorbent element and a moisture barrier. Optionally, and preferably, the panty protector also comprises a protector overwrap. Also optionally, and also preferably, the panty protector is provided with adhesive attachment means. In the figures, the panty protector is indicated by 20, the absorbent element by 21, the moisture barrier by 23, the protector overwrap by 22, and the adhesive attachment means by 24.

The absorbent element can be any absorbent material commonly used in sanitary napkins, disposable diapers, and the like. It can be any of the materials described above as being useful in the absorbent pad of the primary menstrual pad.

As a practical matter, most of the bodily fluids are adsorbed by and are contained within the absorbent pad of the primary menstrual pad. One major function of the panty protector is, as its name implies, to protect the user's garments from soiling by absorbed fluids which may be expelled from the primary menstrual pad or which may inadvertently bypass it. Because the absorbent element performs a different function from that of the absorbent core, the absorbent element can be, and most preferably is, somewhat smaller and less bulky than the absorbent core. In general, the absorbent element will contain at saturation a smaller total quantity of fluid than will the absorbent core.

Because the absorbent element has different requirements than does the absorbent core, it can be formed of different materials. For example, single or multiple plies of paper tissue as commonly used in paper toweling or toilet tissue can be used to form the absorbent element. Preferably, the absorbent element is formed of from about 1 to about 5 plies of paper tissue.

Paper tissue comprising one or more plies having a basis weight of from about 24 to about 48 grams per square meter and an apparent density of from about 0.10 to about 0.12 grams per cubic centimeter as made by the process described in U.S. Pat. No. 3,301,746 which issued to Sanford and Sisson on Jan. 31, 1967 (which patent is herein incorporated by reference) has been found to be quite satisfactory for use in this invention. Wet strength resins and latex binders can be, and preferably are, used to provide additional strength to the paper tissue used in the absorbent element.

Paper tissue made by the process described in U.S. Pat. No. 3,994,771 which issued to Morgan et al on Nov. 30, 1976, herein incorporated by reference, can also be used to good advantage in the absorbent element.

In addition to the absorbent element, the panty protector comprises a moisture barrier. The moisture barrier underlays the absorbent element. That is, the moisture barrier is placed adjacent the absorbent element in such a manner that the absorbent element is interposed between the moisture barrier and the primary menstrual pad. In use, the moisture barrier is interposed between the absorbent element and the user's garments. The function of the moisture barrier is, as its name implies, to prevent fluids which may be expelled from or which may inadvertently bypass the primary menstrual pad from contacting and soiling the user's garments. Any flexible, moisture impervious material can be used to construct the moisture barrier. Examples of suitable materials are films of thermoplastics such a polyethylene and polypropylene and films of natural and synthetic rubbers. Preferably, the moisture barrier is formed of low density polyethylene films having a thickness of from about 0.012 to about 0.06 millimeter.

In certain embodiments to be discussed below, the protector overwrap can function as the moisture barrier. Embodiments comprising a discrete moisture barrier and moisture barriers functionally provided by the overwrap are equivalent for the purposes of this specification.

Figure 1:
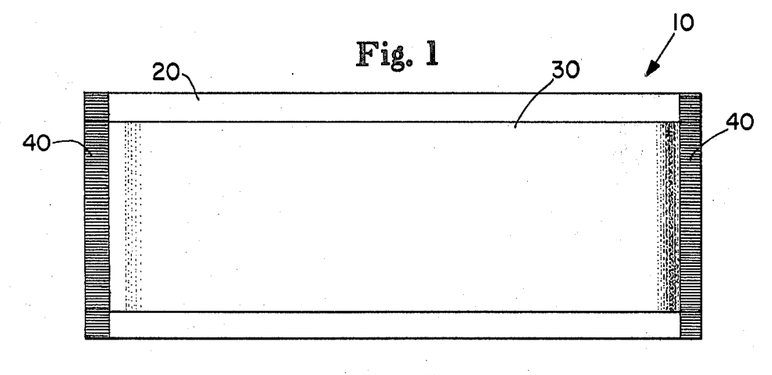
FIG. 1 is a plan view of one embodiment of the compound sanitary napkin of this invention.
Figure 2:
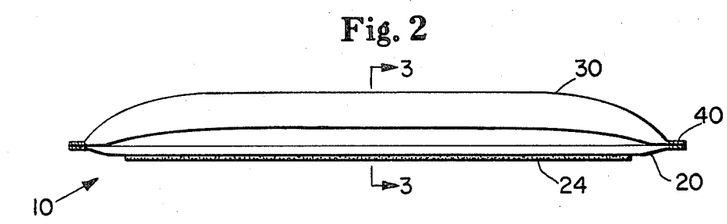
FIG. 2 is a side elevation view of the compound sanitary napkin shown in FIG. 1.
Figure 3:
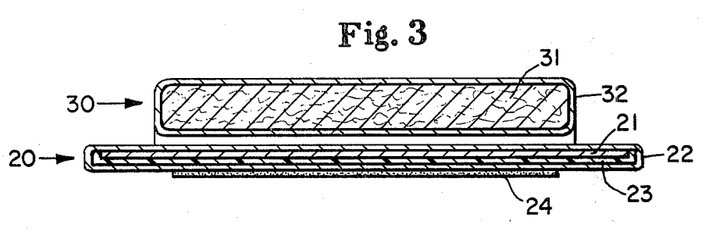
FIG. 3 is a cross sectional view of the compound sanitary napkin shown in FIGS. 1 and 2 as taken along line 3—3 of FIG. 2.

As shown in the figures, the panty protector can be of generally rectangular shape. Its thickness, as shown in cross-section in FIGS. 3 and 5, is generally somewhat less than its width. However, the panty protector is not limited to rectangular shapes inasmuch as ovals, elipsoids and the like are also useful.

Preferably, the panty protector is about the same length as the primary menstrual pad and is essentially at least as wide as the primary menstrual pad in the unstressed condition. It is quite possible for the panty protector to be somewhat longer than the primary menstrual pad and still function effectively. In this situation, the panty protector will extend beyond the union means rather than terminating in the vicinity thereof as shown in the figures.

In addition to the absorbent element and the moisture barrier, the panty protector can optionally, and preferably, be supplied with a protector overwrap.

The protector overwrap can be any of the materials described above as being useful for the pad overwrap. In addition to providing a soft, smooth surface which may incidently contact the user's skin, the protector overwrap enhances the aesthetic characteristics of the compound sanitary napkin of this invention. In addition, in certain embodiments the protector overwrap can function as a moisture barrier as discussed more fully hereinafter.

In the embodiment of the compound sanitary napkin illustrated in FIG. 3, protector overwrap 22 completely encases absorbent element 21 and moisture barrier 23. In the embodiment illustrated in FIG. 5, protector overwrap 22 completely encases absorbent element 21 but is interposed between absorbent element 21 and moisture barrier 23. Preferably, the former configuration is used.

As noted above, certain materials which can be used for the protector overwrap can also function as the moisture barrier. The apertured films described in detail hereinbefore are such materials. When they are constructed as discussed, they will function both as the protector overwrap (i.e., fluids will pass through them in one direction) and as the moisture barrier (i.e. fluids will not readily pass through them in the reverse direction).

Optionally, and preferably, the panty protector is provided with adhesive attachment means. The attachment means can be any convenient material such as the adhesives commonly used in the sanitary napkin art to secure sanitary napkins to the inner crotch area of the user's undergarments. It is affixed to the panty protector by any convenient means on the outermost surface thereof and adjacent that face which is opposite the face disposed toward the primary menstrual pad. Normally, the exposed adhesive surface of the attachment means is covered with a release tape as is well known to those skilled in the sanitary napkin art. The function of the protective release tape, which is not shown in the figures, is to cover the adhesive attachment means and prevent its adhering to packaging materials or other surfaces until such time as the user affixes the compound sanitary napkin to her undergarment.

While it is preferred that the compound sanitary napkin be affixed to the user's undergarments through the agency of adhesive attachment means, it can be so affixed by any other convenient method such as the use of safety pins. Optionally, but not preferably, the compound sanitary napkin can be supported adjacent the user's crotch area through the agency of a conventional sanitary napkin supporting belt. In this latter circumstance, the compound sanitary napkin can be affixed to the supporting belt by any convenient means. In this latter circumstance, the physical comfort of the compound sanitary napkin may be decreased.

To form the compound sanitary napkin of this invention, the primary menstrual pad and the panty protector are joined by union means having limited extent.

The precise nature of the union means is immaterial so long as the union means selected serves to join the primary menstrual pad and the panty protector into the compound sanitary napkin of this invention with sufficient tenacity that the primary menstrual pad and the panty protector are not disconnected during use. Union means such as adhesive attachment with well known hot melt adhesives and sewing are quite satisfactory. If the natures of the components selected to construct the constituents of the compound sanitary napkin so permit, heat welding, ultrasonic welding, or a combination of both heat and ultrasonic welding can be used.

While the precise nature of the union means is immaterial, the extent of the attachment between the primary menstrual pad and the panty protector is critical to the functioning of the compound sanitary napkin.

As used herein, the term "union means having limited extent" designates a means for firmly attaching each end of the primary menstrual pad to the corresponding end of the panty protector in such a manner that the two components are free to move relative to one another along essentially their entire common length. The two components are free to move with respect to one another along essentially their entire common length when, in use, a continuous section of at least about 75% (by length) of their common length is uninterrupted by points of attachment between the two constituents.

The immediately preceding description of the union means of limited extent describes the situation in which the corresponding ends of the primary menstrual pad and the panty protector are joined one to another. (This is the embodiment illustrated in the figures.) It is to be understood that the use of the term "end" in this connection does not necessarily mean the exact literal end of the constituent under discussion. The term "end" is to be construed to refer to that general region adjacent the effective end of the constituent under discussion. For example, the preceding discussion indicated that the panty protector may have a length substantially greater than that of the primary menstrual pad. In this situation, should the primary menstrual pad be superimposed on the panty protector and adjacent the center thereof and joined thereto by union means at each end of the primary menstrual pad, the points of attachment will be some distance from the literal ends of the panty protector. However, for purposes of this specification, such a situation would result in the ends of the primary menstrual pad being attached to the effective ends of the panty protector. As another example, it is possible for the optional pad overwrap placed about the absorbent core to extend beyond each end of the absorbent core. The primary menstrual pad could then be joined to the panty protector by union means located adjacent the actual end of the absorbent core, but such union means would be located some distance from the actual ends of the optional pad overwrap. In this situation, the effective ends of the primary menstrual pad would be joined to the effective ends of the panty protector even though a portion of pad overwrap material extends beyond the locus of the union means.

Figure 4:
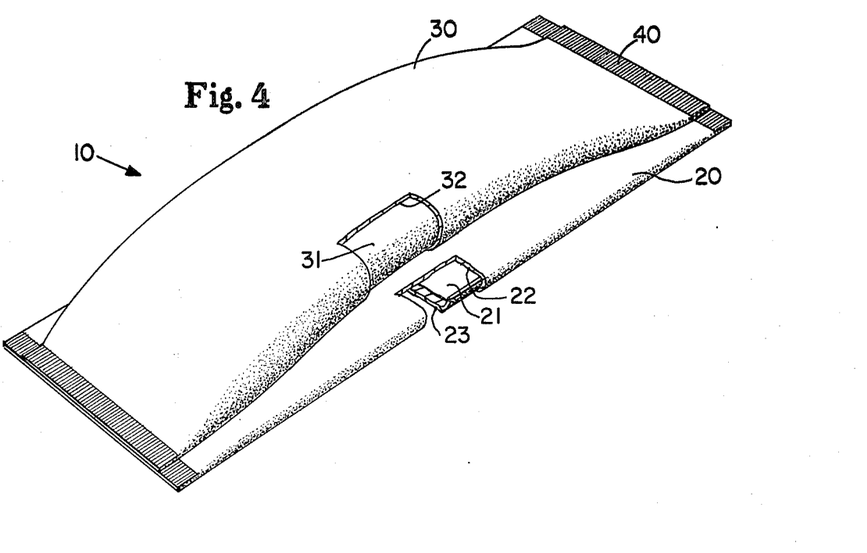
FIG. 4 is a partially cutaway perspective view of the embodiment of the compound sanitary napkin shown in FIGS. 1 and 2 wherein the spatial relationship between the constituents has been altered to clearly show the limited extent of the union means.

The compound sanitary napkin of this invention, as hereinbefore described in detail, performs its intended function of absorbing menses and other bodily fluid more effectively and efficiently than heretofor known sanitary napkins, provides greater protection from soiling of the user's garments than do previously known sanitary napkins, and can be worn by the user with greater physical comfort than can previously known sanitary napkins. Without being bound by any theory of operation, it can be suggested that the improved functioning of the compound sanitary napkin relative to previously known sanitary napkins is attributable to the use of the two constitutents (the primary menstrual pad and the panty protector) joined by union means having limited extent. FIG. 4 is a cutaway perspective view of the compound sanitary napkin shown in FIGS. 1 and 2 wherein the relative positions of the constituents 20 and 30 are as if the two union means having limited extent 40 have been displaced toward one another thereby causing the mid portions of primary menstrual pad 30 and panty protector 20 to be displaced relative to one another. This figure clearly illustrates the relative freedom of motion between the two constituents which exists when union means having limited extent are employed.

In use, the panty protector is normally secured to the user's undergarments where it is subjected to latitudinal and longitudinal compressive and expansive forces produced as the user moves. Compressive forces are exerted on both constituents by the user's body motion, generally by the user's legs. Expansive forces can be exerted on the panty protector by means of the undergarment to which it is attached. The primary menstrual pad, however, by virtue of its attachment to the panty protector by union means having limited extent, is free to move independently of the panty protector. While it can not avoid some of the same compressive forces applied to the panty protector, it can in this state of relative freedom avoid some of the deleterious expansive forces applied to the panty protector. This avoidance of cyclical compression and expansion tends to avoid the loss of absorbent capacity normally experienced by absorbent bodies as they are compressed and expanded thereby providing a more efficient reservoir for containing bodily fluids. The panty protector, on the other hand, tends to serve to capture bodily fluids occasionally expelled from the primary menstrual pad, is not intended to absorb large quantities of fluid, and can easily withstand compression and reexpansion without being detrimentally affected to any practical extent. At the same time, the union means having limited extent serve to maintain the primary menstrual pad in its proper location adjacent the user's crotch region. The flexibility of the panty protector and its low bulk also serve to enhance the protection from soiling afforded the user's garments. As the user's movements cause her undergarment to compress, wrinkle, and reexpand, the low bulk and flexibility of the panty protector allow it to remain associated with her undergarment and to compress, wrinkle, and reexpand with it thereby remaining in position to absorb bodily fluids expelled by or bypassing the primary menstrual pad.

The compound sanitary napkin has been described primarily in terms of a device to absorb and contain menses and other vaginal discharges. While this is the principal use of such a device, it can also be used to absorb urine as discharged by incontinent females.

In order to more fully describe the compound sanitary napkin of this invention, and not by way of limitation, the following examples are presented.

EXAMPLE I

A compound sanitary napkin of this invention was constructed from the following materials:

In the primary menstrual pad, the absorbent core was formed of carded polyester fibers sold under the tradename T-54W Dacron Staple by E. I. DuPont de Nemours & Company of Wilmington, Delaware. The fibers had a cut length of about 3.8 centimeters, were about 1.5 denier, and had about 45% crimp. Prior to carding, the fibers were thoroughly washed in a 0.05% by weight solution of Pluronic P-84 (a nonionic surfactant manufactured by BASF Wyandotte of Wyandotte, Michigan) and 0.05% tetrasodium pyrophosphate. (It should be noted that washing of the fibers is not normally considered to be a necessary step in the process of making the compound sanitary napkin of this invention. The particular fibers used in this example were commercially available fibers having an unknown, to the inventor, finish applied thereto. It was deemed expedient to remove the unknown finish and then to treat the fibers as noted hereinafter to render the fiber surfaces hydrophilic. It is to be expected that fibers will be available commercially either having the desired finish thereon or being completely free of finish. In the event that it is not possible to obtain fibers having a proper finish and surface characteristics, the fibers will be preferably washed prior to further processing and incorporation into compound sanitary napkins.) The washed and rinsed fibers were treated with a 10% by weight solution of Pluracol 747 (a nonionic surfactant made by BASF Wyandotte) dissolved in equal volumes of ethanol and distilled water. The fibers were separated from the treatment solution by vacuum filtration and dried at ambient conditions. The optional pad and protector overwraps were used and were fabricated from 0.025 millimeter thick polyethylene film which was provided with pentagonal apertures having a maximal diagonal of about 0.08 centimeter and an open area of about 45%. In addition, the surfaces of the overwraps which were disposed toward the absorbent core and the absorbent element were provided with an essentially uniform covering of approximately 20 grams per square meter of mixed softwood pulp fibers secured thereto by a pressure sensitive latex adhesive sold under the designation CA-5885X by Century Adhesives Co. of Columbus, Ohio. The adhered pulp fibers were treated with L-92 surfactant from 5% (by weight) ethanol solution so that each pad overwrap and each protector overwrap, as described below, contained about 0.003 gram surfactant associated with the pulp fibers.

In the panty protector, the absorbent element comprised two sheets of a commercially available two-ply tissue paper towel product having a basis weight of approximately 26 grams per square meter so sold under the Bounty trademark by Procter & Gamble of Cincinnati, Ohio. The protector overwrap was the same material described above for the pad overwrap. In this embodiment, the protector overwrap functioned as the moisture barrier. The panty protector was provided with adhesive attachment means comprising hot melt pressure sensitive adhesive sold under the tradename Instant Lok 34-2823 by National Starch Co. of Bridgewater, New Jersey, which had been extruded onto a silicone treated release paper prior to association with the protector overwrap.

Three grams of carded polyester fibers were placed on a rectangular section of pad overwrap material measuring approximately 14 centimeters by 25.4 centimeters. (The fibers adhered to the pad overwrap were oriented toward the polyester fibers.) The polyester fibers were formed into an absorbent core by spreading them in an essentially uniform thickness layer approximately 15.9 centimeters long by 5 centimeters wide. The overwrap material was folded about the absorbent core and heat welded with a longitudinal seam to form the primary menstrual pad.

Two sheets of paper tissue toweling material each approximately 17.1 centimeters by 7.6 centimeters were placed in the center of a rectangular section of protector overwrap material measuring approximately 19 centimeters by 25.4 centimeters. (The fibers adhered to the protector overwrap material were oriented toward the absorbent element.) The protector overwrap was carefully folded about the absorbent element and heat welded with a longitudinal seam to form the panty protector.

The assembled panty protector was placed on a flat surface with the longitudinal seam facing downwardly. The assembled primary menstrual pad was placed on the panty protector with the seam oriented toward the panty protector and the longitudinal axes of the two constituents parallel. Union means having limited extent were used to join the two constituents. In this example, the union means comprised two narrow heat welds each extending laterally across the two constituents with one adjacent each end of the absorbent core and between the absorbent core and the end of the protector overwrap. Excess overwrap material was trimmed from each end of the primary menstrual pad and the panty protector as near the heat seal as possible. The resulting compound sanitary napkin was approximately 18.4 centimeters long and 7.9 centimeters wide.

The release tape and adhesive attachment means were applied to the underside (seam-side) of the panty protector.

The assembled unit was sterilized by ethylene oxide treatment before use.

The resulting product was absorbent, provided protection from soiling, and was judged by users to be physically comfortable.

EXAMPLE II

A second embodiment of the compound sanitary napkin of this invention was constructed as in Example I with the following differences:

The absorbent core was formed of comminuted and airlaid southern softwood fluff pulp which was formed into a rectangle measuring approximately 5.1 centimeters by 17.8 centimeters weighing approximately 5 grams and having a density of approximately 0.06 gram per cubic centimeter. The pad overwrap and the protector overwrap were formed of the same apertured film used in Example I, but neither had the layer of fibers adhered to the inner surfaces thereof. The absorbent core and the absorbent elements were adhesively affixed to, respectively, the inner surfaces of the pad overwrap and the protector overwrap before the overwraps were heat welded with longitudinal seams. The absorbent element was approximately 7.6 centimeters by 17.8 centimeters. The finished product was approximately 20.3 centimeters long by 7.9 centimeters wide. After assembly, the upper surface of the compound sanitary napkin was essentially uniformly treated with about 0.005 gram L-92 from 5% (by weight) ethanol solution and, after the ethanol had evaporated, about 0.001 gram No. #1745 U.S.P. grade talc made by Whittaker, Clark & Daniels, Inc. of South Plainfield, New Jersey.

As did the product of Example I, the product of Example II was absorbent, provided protection from soiling and, was judged by users to be physically comfortable.

What is claimed is:

1. A compound sanitary napkin comprising an elongate primary menstrual pad having two oppositely disposed ends and an elongate panty protector having two oppositely disposed ends wherein: (a.) said primary menstrual pad comprises a fibrous absorbent core; (b.) said panty protector comprises an absorbent element and a moisture barrier; and (c.) each of said ends of said primary menstrual pad is firmly affixed to the corresponding end of said panty protector by union means having limited extent in such a manner that there exists a continuous section comprising at least about 75% by length of the common length of said primary menstrual pad and said panty protector which section is uninterrupted by points of attachment between said primary menstrual pad and said panty protector.

2. The compound sanitary napkin of claim 1 wherein said primary menstrual pad comprises a pad overwrap.

3. The compound sanitary napkin of claim 2 wherein said panty protector comprises a protector overwrap.

4. The compound sanitary napkin of claim 1 wherein said panty protector comprises a protector overwrap.

5. The compound sanitary napkin of claim 1, 2, 3, or 4 wherein said panty protector comprises adhesive attachment means.

6. The compound sanitary napkin of claim 5 wherein said primary menstrual pad comprises a fluid barrier.

7. The compound sanitary napkin of claim 1, 2, 3, or 4 wherein said absorbent core comprises wood pulp fibers.

8. The compound sanitary napkin of claim 7 wherein said panty protector comprises adhesive attachment means.

9. The compound sanitary napkin of claim 1, 2, 3, or 4 wherein said absorbent core comprises an unbonded array of nonabsorbent, hydrophilic, resilient, moisture insensitive fibers.

10. The compound sanitary napkin of claim 9 wherein said panty protector comprises adhesive attachment means.

11. The compound sanitary napkin of claim 1, 2, 3, or 4 wherein said absorbent element comprises wood pulp fibers.

12. The compound sanitary napkin of claim 11 wherein said panty protector comprises adhesive attachment means.

13. The compound sanitary napkin of claim 1, 2, 3, or 4 wherein said absorbent element comprises at least one ply of paper tissue.

14. The compound sanitary napkin of claim 13 wherein said panty protector comprises adhesive attachment means.

15. The compound sanitary napkin of claim 2, 3, or 4 wherein said pad overwrap and said protector overwrap comprise non-woven fabric.

16. The compound sanitary napkin of claim 2, 3 or 4 wherein said pad overwrap and said protector overwrap comprise apertured film.

17. The compound sanitary napkin of claim 16 wherein said apertured film comprises a thermoplastic film having a caliper less than about 0.075 centimeter, an open area of at least about 35%, and wherein said apertures are irregular and at least about 25% of said apertues have an equivalent hydraulic diameter smaller than about 0.064 centimeter wherein said film functions as a moisture barrier and as a fluid barrier.

18. The compound sanitary napkin of claim 2 or 3 wherein said protector overwrap comprises an apertured film having a caliper less than about 0.075 centimeter, an open area of at least about 35%, and wherein said apertures are irregular and at least about 25% of said apertures have an equivalent hydraulic diameter smaller than about 0.064 centimeter and wherein said film functions as said overwrap and as said moisture barrier.

19. The compound sanitary napkin of claim 16 wherein said apertured film comprises a thermoplastic film provided with a multiplicity of protuberances having a base in the plane of said overwrap and an apex remote from said plane, wherein essentially each of said protuberances is provided with an aperture having a maximal diagonal of from about 0.025 centimeter to about 0.025 centimeter, and wherein essentially each base is provided with an aperture having a maximal diagonal at least as great as said maximal diagonal of said respective apex aperture, and herein the caliper of said film is from about 0.033 to about 0.089 centimeter wherein said film functions as a moisture barrier and as a fluid barrier.

20. The compound sanitary napkin of claim 2 or 3 wherein said protector overwrap comprises an apertured thermoplastic film provided with a multiplicity of protuberances having a base in the plane of said overwrap and an apex remote from said plane, wherein essentially each of said protuberances is provided with an aperture having a maximal diagonal of from about 0.025 centimeter to about 0.25 centimeter, and wherein essentially each base is provided with an aperture having a maximal diagonal at least as great as said maximal diagonal of said respective apex aperture, and wherein the caliper of said film is from about 0.033 to about 0.089 centimeter and wherein said film functions as said overwrap and as said moisture barrier.

21. The compound sanitary napkin of claim 2, 3 or 4 whereins said absorbent core comprises wood pulp fibers; said absorbent element comprises at least one ply of paper tissue; said pad overwrap and said protector overwrap comprise apertured thermoplastic film having a caliper less than about 0.075 centimeter, an open area of at least about 35%, and wherein said apertures are irregular and at least about 25% of said apertures have an equivalent hydraulic diameter smaller than about 0.064 centimeter wherein said film functions as a moisture barrier and as a fluid barrier.

22. The compound sanitary napkin of claim 21 wherein said overwraps are provided with a layer of uniformly distributed fibers affixed thereto, said uniformly distributed fibers being less hydrophobic than said overwrap.

23. The compound sanitary napkin of claim 21 wherein said panty protector comprises adhesive attachment means.

24. The compound sanitary napkin of claim 24 wherein said overwraps are provided with a layer of uniformly distributed fibers affixed thereto, said uniformly distributed fibers being less hydrophobic than said overwrap.

* * * * *

UNITED STATES PATENT AND TRADEMARK OFFICE
CERTIFICATE OF CORRECTION

PATENT NO. : 4,425,130
DATED : January 10, 1984
INVENTOR(S) : THOMAS A. DES MARAIS It is certified that error appears in the above-identified patent and that said Letters Patent is hereby corrected as shown below:

In Column 1 at line 9 delete "woven" and insert therefor --woman--
In Column 1 at line 21 delete "body-containing" and insert therefor --body-contacting--
In Column 2 at line 6 delete "an" and insert therefor --and--
In Column 2 at line 13 delete "adsorbent" and insert therefor --absorbent--
In Column 3 at line 56 delete "communition" and insert therefor --comminution--
In Column 4 at line 55 delete "0.003" and insert therefor --0.03--
In Column 5 at line 42 delete "maximum" and insert therefor --maximal--
In Column 6 at line 66 delete "a" and insert therefor --as--
In Column 10 at line 63 delete "so" and insert therefor --as--
In Claim 19 in Column 13 at line 31 delete "0.025", which is the second occurrence of "0.025" in said Claim 19, and insert therefor --0.25--
In Claim 19 in Column 13 at line 36 delete "herein" and insert therefor --wherein--

Signed and Sealed this

Thirtieth Day of September 1986

[SEAL]

Attest:

DONALD J. QUIGG

Attesting Officer

Commissioner of Patents and Trademarks